(12) United States Patent
Silverstone

(10) Patent No.: US 6,351,674 B2
(45) Date of Patent: Feb. 26, 2002

(54) METHOD FOR INDUCING ELECTROANESTHESIA USING HIGH FREQUENCY, HIGH INTENSITY TRANSCUTANEOUS ELECTRICAL NERVE STIMULATION

(75) Inventor: Leon M. Silverstone, San Diego, CA (US)

(73) Assignee: Synaptic Corporation, Aurora, CO (US)

( * ) Notice: Subject to any disclaimer, the term of this patent is extended or adjusted under 35 U.S.C. 154(b) by 0 days.

(21) Appl. No.: 09/778,244

(22) Filed: Feb. 6, 2001

Related U.S. Application Data

(63) Continuation-in-part of application No. 09/691,626, filed on Oct. 18, 2000, now abandoned, which is a continuation of application No. 09/199,073, filed on Nov. 23, 1998, now Pat. No. 6,161,044.

(51) Int. Cl.[7] ................................. A67N 1/36
(52) U.S. Cl. ........................................ 607/46
(58) Field of Search ............................ 600/554; 607/46

(56) References Cited

U.S. PATENT DOCUMENTS

| | | | |
|---|---|---|---|
| 4,550,733 A | 11/1985 | Liss et al. | 128/421 |
| 4,924,880 A | 5/1990 | O'Neill et al. | 128/787 |
| 5,052,391 A | 10/1991 | Silverstone et al. | 128/422 |

Primary Examiner—William E. Kamm
(74) Attorney, Agent, or Firm—Fitch, Even, Tabin, Flannery

(57) ABSTRACT

A non-invasive method of treating, controlling or preventing medical, psychiatric or neurological disorders is provided using transcutaneous electrical stimulation. A plurality of stimulation frequency parameters are used ranging from a relatively high frequency, for example about 40,000 Hertz, to a relatively low frequency, for example about 250 Hertz. The entirety of frequency parameters may be administered at each of a plurality of stimulation intensity levels. In particular, stimulating may begin at a first highest frequency parameter and a first lowest intensity parameter with the stimulation frequency parameter incrementally decreasing to the lowest frequency parameter. Then the frequency parameter is returned to the highest frequency parameter, and the intensity parameter increased to a next higher intensity parameter, and again stimulating through the plurality of frequency parameters from the highest frequency to the lowest frequency. The method described herein is useful in treating, controlling and/or preventing various disease states and disorders, and has been found to be particularly effective in administering nerve block electroanesthesia.

10 Claims, 4 Drawing Sheets

EPI - Epinephrine (pg/ml)
Norep - Norepinephrine (pg/ml)
ACTH - Adrenocorticotropic hormone (pmol/l)
SE - Serotonin (ng/ml)
BE - Beta Endorphin (pg/0.1 ml)

METHOD FOR INDUCING ELECTROANESTHESIA USING HIGH FREQUENCY, HIGH INTENSITY TRANSCUTANEOUS ELECTRICAL NERVE STIMULATION

This application is a continuation-in-part of U.S. Ser. No. 09/691,626, filed Oct. 18, 2000, abandoned, which was a continuation of U.S. Ser. No. 09/199,073, filed Nov. 23, 1998, now U.S. Pat. No. 6,161,044, the disclosures of both of which are expressly incorporated by reference.

FIELD OF THE INVENTION

The present invention relates to improved methods for the non-invasive treatment of various disease conditions using an improved process of transcutaneous electrical stimulation. In particular, provided herein are improved methods of non-invasively treating symptoms of tremor disorders including essential tremors and tremors associated with Parkinson's Disease; symptoms of dementia disorders including cortical dementia, such as is found in Alzheimer's disease and Pick's disease, subcortical dementia, such as is found in Parkinson's disease, Huntington's chorea and supranuclear palsy, and multi-infarct dementia; and symptoms of painful degenerative disorders, such as fibromyalgia and reflex sympathetic dystrophy by using transcutaneous electrical nerve stimulation programs of variable intensity and variable frequency. Also provided are apparatus for performing such methods.

BACKGROUND OF THE INVENTION

Transcutaneous electrical nerve stimulation (TENS) is a well known medical treatment used primarily for symptomatic relief and management of chronic intractable pain and as an adjunctive treatment in the management of post surgical and post traumatic acute pain. TENS involves the application of electrical pulses to the skin of a patient, which pulses are generally of a low frequency and are intended to affect the nervous system in such a way as to suppress the sensation of pain that would indicate acute or chronic injury or otherwise serve as a protective mechanism for the body. Typically, two electrodes are secured to the skin at appropriately selected locations. Mild electrical impulses are then passed into the skin through the electrodes to interact with the nerves lying thereunder. As a symptomatic treatment, TENS has proven to effectively reduce both chronic and acute pain of patients. However, TENS has shown no capacity for curing the causes of pain, rather the electrical energy simply interacts with the nervous system to suppress or relieve pain.

The human nervous system essentially serves as a communication system for the body wherein information concerning the state of the body is communicated to the spinal cord (and/or brain) and behavioral instructions are communicated from the brain (and/or spinal cord) to the rest of the body. Thus, there are ascending neural pathways, such as the ascending pain pathways, and descending neural pathways, such as the descending inhibitory pathway (DIP), within the nervous system.

Briefly, pain impulses received by the free nerve endings of nociceptive nerve fibers (in particular, Aδ and C fibers) are conducted, through various synapses, to the brain. In particular, these first order neurons enter the dorsal horn of the spinal cord and synapse with second order neurons, which are either relay cells, projecting into the brain stem or thalamus, or interneurons, synapsing to other interneurons or to relay cells. The second order neurons then (mostly) cross the spinal cord and become the anterolateral system, comprised of the neospinothalamic tract (or lateral spinothalamic tract) and paleospinothalamic tract. The nerve fibers of the anterolateral system then terminate in various regions of the brain, including the brain stem, midbrain and thalamus.

Inhibition (or modulation) of pain, by the body, can occur anywhere from the point of origin of the pain through the successive synaptic junctions in the pain's central pathway. For example, following the descending inhibitory pathways (DIP) of pain inhibition/modulation, stimulation in the cerebral cortex of the brain descends to the thalamus and then to the periaqueductal gray (PAG) of the midbrain. The PAG region is rich in opiate receptors responsible for secreting morphine-like enkephalins and endorphins. Nerve fibers from the PAG then descend to the nucleus raphe magnus (NRM) in the brainstem. The NRM is responsible for the secretion of serotonin, a compound that is instrumental in elevating pain threshold levels and combating depression. Fibers from the NRM then descend into the spinal cord, synapsing with other inhibitory interneurons to cause secretion of additional powerful anti-pain neurotransmitters such as gamma-aminobutyric acid (GABA).

While prior art TENS devices and methods have been shown to be capable of affecting the ascending pathways of pain perception, they have shown little or no ability to affect the descending inhibitory pathways of the nervous system. The precise mechanisms by which these prior art TENS methods operate to affect pain are not known; however, one theory suggests that, by producing fast electrical waves that travel up the Aβ nociceptive fibers, the TENS electrical stimulation pulses block pain stimulus traveling up the Aδ and C fibers. One frequently reported problem with the prior art TENS methods is acclimation or accommodation; that is, the patient acclimates to the transcutaneous stimulation and the pain returns. The intensity of the treatment, in such cases, is increased to overcome the patient's accommodation of the treatment, but shortly, a maximum level of intensity is reached and further treatment is ineffective.

A TENS simulator such as that shown in U.S. Pat. No. 5,052,391 is, in effect, an electrical pulse generator which delivers electrical pulses (or impulses), transcutaneously, at a predetermined fixed or variable frequency. Typically, TENS stimulators deliver electrical pulses at frequencies in the range of about 50 to 200 Hertz (Hz). Most commonly, variable frequency TENS devices operate by beginning stimulation at the lowest frequency setting then increasing the frequency of stimulation until a pre-defined event occurs, such as motor nerve response or patient comfort achieved. Such increases in frequency may be controlled by a doctor or other medical personnel or, more often, are controlled by the patient him/herself. In addition to increasing the frequency of the stimulation pulses, the patient may be treated by simultaneously increasing the intensity (or amplitude) of the stimulation output of the device.

For example, the patient may have a choice of different "levels" of stimulation, each sequential level providing an increased frequency and intensity of stimulation as compared to the previous level. In either case, the output parameters generally start at their lowest level and are increased over the duration of the treatment.

Normally, when the patient (or other operator) increases the stimulation level of the TENS machine, in accordance with his/her doctor's instructions, the new, higher level is somewhat uncomfortable at first. However, as the patient knows from experience, his/her body accommodates to the new higher level of stimulation within a tolerable length of time. Once stimulation at one level becomes fully accommodated, that is, no longer works well to relieve the symptoms for which the treatment is being administered, the patient increases the stimulation level. Thus, as mentioned previously, the body is able to adjust to the electrical stimulation, requiring ever increasing levels of stimulation to achieve the same level of pain relief, often until no amount of stimulation is effective. The use of devices of this general type for dental anesthesia is shown in U.S. Pat. Nos. 4,924,880 and 4,550,733. These devices generally employed a biphasic symmetrical sinusoidal waveform at a peak voltage of only 2 volts and a peak current of only 0.87 milliamps.

In some cases, the treatment frequency of the TENS device is fixed by design, or is established as a preselected, generally arbitrary, rate at the time of treatment, and only adjustment of the intensity (or amplitude) of the electrical pulses is allowed. The typical intensity level of TENS stimulators is in the range of 30–200 volts. The waveform characteristic of the electrical pulses varies and includes, for example, symmetrical sinusoidal waveforms, symmetrical biphasic waveforms and DC needle spikes. Generally, the different waveforms are believed to offer some advantage over other waveforms; however, there has been no clear consensus that any particular type of waveform is consistently more advantageous than other types. What is known, however, is the general shape of the action potential waveform that is responsible for producing electrical activity in neurons. Characteristic of this action potential are a very fast rise time and a slow decay.

The precise mechanisms by which transcutaneous electrical stimulation operates to control pain are not known. When used to treat pain, the patch electrodes of the TENS device are generally attached to the patient in the vicinity of the pain. Thus, for example, in treating joint pain, electrodes would be affixed near the joint and stimulation administered thereto. This localized stimulation then affects the nervous system to reduce the patient's perception of pain, presumably by either affecting the pain signals being sent from the region to the brain or by affecting the brain's perception of the signals it is receiving from the region. Even the body's natural mechanisms for perceiving and affecting pain are poorly understood. However, it is known that various biochemicals are released by nerve and brain cells in response to chemical and/or electrical stimulation of those cells. These neurotransmitters assist in the transmission of electrical messages between and within the peripheral and central nervous systems.

In contrast to the TENS devices and methods used to affect the ascending pathways of the nervous system, implantable electrical stimulators have been used to affect descending motor pathways of the nervous system. These electrical stimulators are surgically implanted into the patient's brain in order to affect, by direct electrical stimulation, specific regions of the brain. For example, by implantation of a stimulating electrode into the appropriate brain region, such as the thalamus and/or basal ganglia, nervous activity within the brain can be affected and the symptoms of movement disorders, such as akinesia, bradykinesia or rigidity and hyperkinetic disorders, can be reduced. See for example U.S. Pat. No. 5,716,377, Rise, et al., the entirety of which is hereby incorporated by reference. Thus, by stimulating the brain in this manner, the skeletal muscles at the termination of the descending motor pathway are affected. Obviously, surgical implantation of an electrode into the brain, as well as direct electrical stimulation of the brain are risky procedures that are preferably utilized only in the most extreme cases and after failure of less risky procedures.

Various disease conditions and disorders involve the brain and/or nervous system and thus may be amenable to treatment using drugs and/or electrical stimulation. For example, U.S. Pat. No. 5,716,377, issued to Rise, et al., Feb. 10, 1998, describes a method of treating movement disorders by means of an electrode implanted into the brain of the patient. Similarly, U.S. Pat. No. 5,713,923, issued to Ward, et al., Feb. 3, 1998, describes a method of treating epilepsy using a brain implanted electrode in combination with one or more drugs. While the effects of electrical stimulation of certain specific nerves, specific nerve/brain regions and/or specific muscles to treat different diseases and/or disorders have been described, few if any generalizations have resulted therefrom. That is, it is still very difficult to predict what if any type of nerve stimulation or drug therapy will work for any given disorder.

Essential tremor (E.T.) is a movement disorder afflicting more than 5 million people in the United States alone. This disease, which is the most common adult movement disorder, is about 20 times more prevalent than the tremors associated with Parkinson's Disease and is a poorly understood hereditary disorder. It is estimated that 32 in 1000 persons over the age of 60 years suffers from E.T. About 95% of those with this disease experience tremors, i.e. uncontrollable shaking, in both hands, often rendering the hands useless or near useless. Further, E.T. is the primary cause of head tremors (Titubation), which tremors are not only extremely difficult to treat but are particularly embarrassing and debilitating. In particularly severe cases, E.T. patients have elected to undergo difficult and dangerous brain surgery wherein the part of the brain responsible for the tremors is destroyed. Unfortunately, this surgery can result in the unintended permanent impairment or destruction (i.e., paralysis) of movement speech and/or swallowing functions as well as paraesthesia or tingling sensations in the patient's hands and/or head.

The current treatment of choice for essential tremor is drug therapy. However, an estimated 60% of E.T. patients do not respond to drug therapy and must therefore either live with the condition or resort to more dangerous and more invasive forms of treatment. Even when drug therapy is "successful," it rarely results in diminution of head tremors; rather, only hand tremors may respond to the therapy. Further, the patient's body usually acclimates to the drug therapy, requiring increased dosages of drugs, which, after time, become less effective. This necessitates frequent changes in drugs in order to obtain or maintain the same level of relief.

Prior to 1997, in the U.S.A., the only alternative to drug therapy for the relief of the symptoms of essential tremor was surgical destruction of part of the thalamus, from where the tremors are believed to originate. In 1997, (1995 in Europe), an implantable electronic stimulating device was approved for the treatment of essential tremor. This device is implanted deep into the thalamus of the patient and electrical stimulation of that brain structure is used to control the tremor. However, the device is effective to control tremors only unilaterally, that is in only one hand. Further, the success rate of the device is not great, particularly given the invasive nature of the procedure: with about 67% of 113 Parkinson's disease patients in one study experiencing control of tremors and about 58% of 83 essential tremor patients in the study being relieved. Because almost all essential tremor patients suffer bilateral tremors (tremors in both hands), those wishing to have the brain implant must choose which hand to control, at least unless and until more than one implant may be used simultaneously, a procedure that to date has not been approved. Also, the brain implant has no effect on titubation (head tremor).

A prior art implantable brain stimulation device is described for example in U.S. Pat. No. 5,716,377, issued to Rise, et al. and incorporated herein, in its entirety, by reference. This patent describes the use of an implantable device having the stimulating electrode implanted into the basal ganglia or thalamus of the patient, with the electrode lead passing under the skin of the patient to a pulse generator also implanted subcutaneously. Also described in the '377 patent, is the implantable device including a sensor for sensing the tremors. The sensor is also implanted and is connected to the pulse generator. The brain stimulation device is operated at 0.1 to 20 volts and at a frequency of between 2 to 2500 Hertz. Such devices are expensive, about $10,000 for the device plus about $25,000 for the required surgery, and require replacement of the pulse generator, and hence additional surgery and expense, about every three years.

Like essential tremor and Parkinson's disease, dementia disorders such as Alzheimer's disease are primarily diseases of the brain. Alzheimer's disease is a degenerative disease in which nerve cells within the brain die and their connections deteriorate. It is the most common cause of dementia and is the fourth leading cause of death among adults in the United States. While various causative factors have been postulated, such as heredity, environmental toxins and biochemical changes within the aging body, no specific cause for this disease had been identified.

Alzheimer's patients consistently have abnormally low levels of neurotransmitters in their brains, particularly a neurotransmitter known as acetylcholine. This reduction in neurotransmitters results in the gradual deterioration of the patient's mental processes and intellectual functioning, including memory loss, especially short-term memory, behavioral changes, inability to properly use language and the inability to perform skilled activities. Autopsies of Alzheimer's patients reveal the formation of protein plaques, comprised primarily of beta-amyloid protein, within the critical memory and learning centers of the brain. Studies on rats have demonstrated that injection of substance P can block the nerve damage caused by beta-amyloid, and thus, a significant portion of research efforts aimed at controlling this disease have focused on this and other brain biochemicals.

Presently, there is no cure or prevention for Alzheimer's disease. However, two different drugs have been approved in the United States for use in the management of this disease. While neither drug has been proven to provide long term relief from the degenerative process of Alzheimer's, at least one of the drugs has recently demonstrated an ability to stop the decline in memory and alertness for 84% of patients studied for a six month period. Further this drug, known as Aricept (produced by Eisai, a Japanese company), does not apparently cause the liver-toxic side effects seen with the other approved drug. Thus, research on drug therapies for the treatment of Alzheimer's disease continue.

Recently, the treatment of dementia disorders by electrical stimulation of specific cranial nerves has been described. U.S. Pat. No. 5,269,303, issued to Wernicke, et al., Dec. 14, 1993, describes stimulation of the vagus nerve to treat patients with dementia, and U.S. Pat. No. 5,540,734, issued to Zabara, Jul. 30, 1996, describes stimulation of one or both of the trigeminal and glossopharyngeal nerves to treat a variety of neurological, medical and psychiatric disorders, including dementia disorders. Each of these patents are hereby incorporated by reference in their entirety. Unfortunately, however, these methods are premised upon implantation of stimulation electrodes directly onto the specified nerve. This not only means that the patient must undergo major surgery to receive treatment, but also that the scope of treatment will be limited to the specific nerves upon which the electrode is implanted. Thus, once implanted, should the device not work to relieve the symptoms of the dementia or, worst, should the nerve stimulation result in intolerable side effects, either the device must be surgically explanted or must be deactivated and left within the patient's body.

Thus, what is needed is an inexpensive non-invasive method of treating neurology-related disorders, such as dementia disorders and/or movement disorders, that will be effective to relieve the very severe symptoms associated therewith. In particular, with respect to movement disorders, such as essential tremor and tremors associated with Parkinson's disease, methods of providing relief for both bilateral hand tremors and head tremors is needed. Similarly, with respect to dementia disorders, such as Alzheimer's disease, even a slowing of the deterioration associated with the disorders would be welcomed. Also desired is an improved way of creating nerve blocks through the use of electroanesthesia so as to provide a patient with localized comfort when pain would otherwise be experienced.

SUMMARY OF THE INVENTION

The present invention addresses these and other objectives by providing methods for the non-invasive treatment, control and/or prevention of various disease conditions and disorders using transcutaneous electrical stimulation, wherein a plurality of stimulation intensities and a plurality of stimulation frequency parameters are employed such that the entire plurality of frequency parameters is administered, from highest to lowest frequency, at each of the plurality of stimulation intensity parameters. Further provided herein are apparatus for employing these methods.

In one aspect, the present invention provides improved results in the treatment of various diseases by affecting the descending inhibitory pathways and neurotransmitter production and release within the nervous system. In particular, such results are achieved via transcutaneous nerve stimulation, a method which heretofore had not been described or demonstrated, and which has also been found to be effective to administer nerve block electroanesthesia.

In a preferred embodiment, the method contemplated herein, is useful to treat, control and/or prevent tremor disorders, such as essential tremor and tremors associated with Parkinson's disease, dementia disorders, such as Alzheimer's disease, and cortical, subcortical and multi-infarct dementia and painful degenerative disorders, such as fibromyalgia and reflex sympathetic dystrophy. This preferred method involves stimulating at a first highest frequency parameter and lowest intensity parameter; decreasing the frequency parameter to the lowest frequency parameter over the course of time and in a specified manner, while holding the intensity parameter constant. The next stage in treatment is to increase the stimulation frequency parameter back to the highest frequency parameter but at a next higher stimulation intensity parameter. The stimulation frequency parameter is then decreased in the same manner as previously done for the lower intensity parameter; while the intensity parameter is maintained at this next highest level.

The apparatus contemplated for use herein is a high frequency, high intensity transcutaneous electrical nerve stimulator (TENS) similar to that described in U.S. Pat. No. 5,052,391 ('391 patent), issued to Silverstone, et al., the entirety of which patent is hereby incorporated by reference. In a preferred embodiment, the TENS device described in the '391 patent is modified to include a programmable microprocessor capable of retaining and executing at least one, and preferably a plurality, of stimulation programs according to the new methods described herein and further is a digital device instead of analog as described in the '391 patent. Most preferably then, the improved TENS device contemplated herein may be programmed to administer an entire regimen of therapy to a patient without requiring any control on the part of the patient, while still permitting the patient the opportunity to control the device if desired. Further, the device will preferably be able to administer a plurality of treatment regimens, thereby being useful for a plurality of different disease states and disorders.

BRIEF DESCRIPTION OF THE DRAWINGS

Additional aspects, features and advantages of the present invention will be apparent to those of skill in the art upon reading the following detailed description and referring to the accompanying drawings in which like numbers refer to like parts throughout and in which.

DETAILED DESCRIPTION OF THE INVENTION

Figure 1:
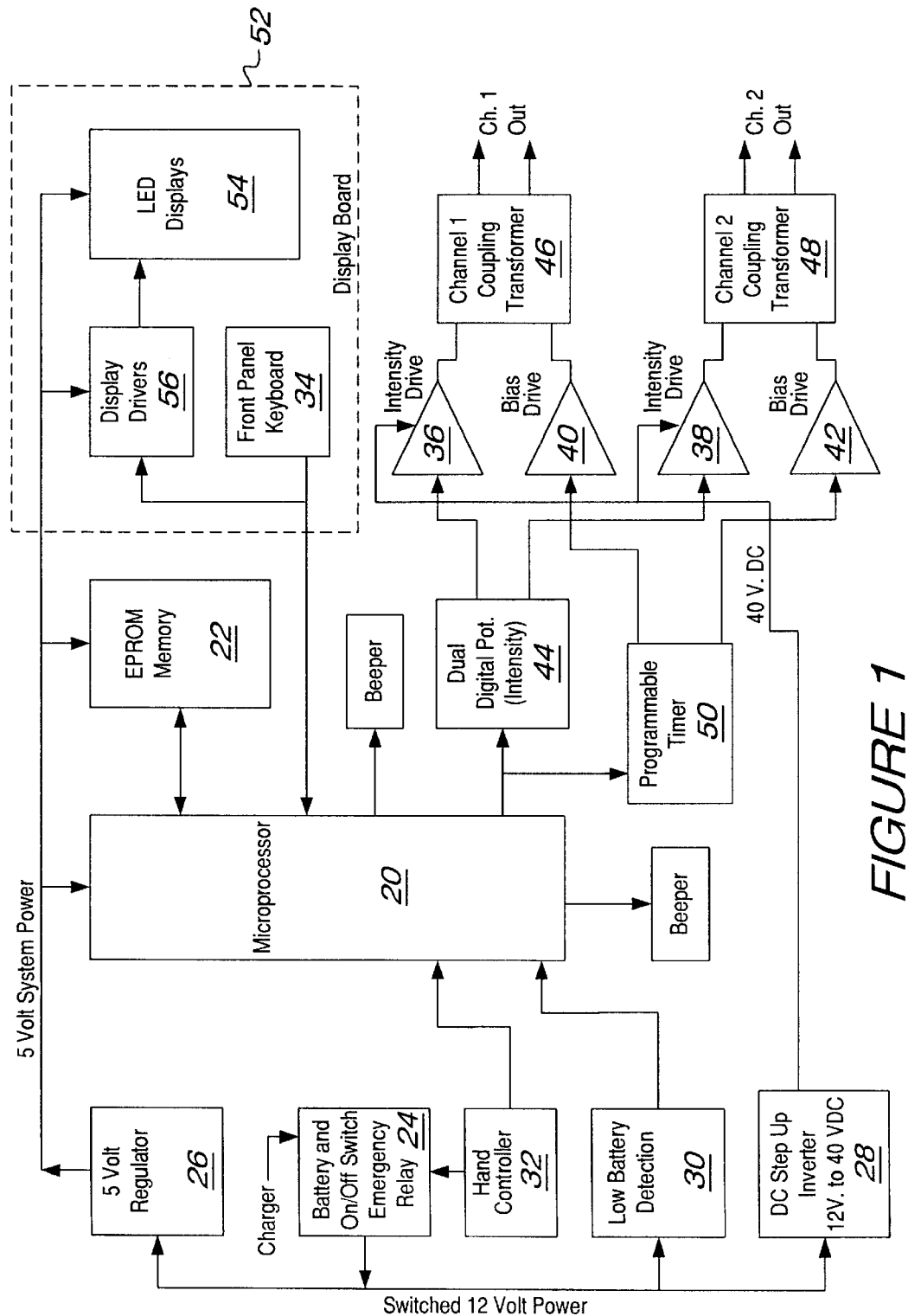
FIG. 1 is a block diagram of a preferred transcutaneous neurostimulator for use in accordance with the methods described herein.

The nervous system, including the brain, operates as a communication network for the body, carrying information and instructions from the brain to the rest of the body, from the rest of the body to the brain and within the nervous system itself. In performing these functions, the nervous system and brain, among other things, use certain biochemical messengers, known as neurotransmitters, to accomplish this transferring of information and instructions. It has been known for some time that electrical stimulation of nerves, for example by implantation of a stimulating electrode onto a particular nerve, can result in release of one or more neurotransmitters from nerve cells thereby affecting the operation of this communication system.

Numerous disease states and disorders involve the nervous system and/or brain, many of which are believed to affect or result from the activity or lack of activity of neurotransmitters. For example, tremor disorders such as essential tremor and Parkinson's disease, dementia disorders, such as cortical dementia, as is found in Alzheimer's disease and Pick's disease, subcortical dementia, as is found in Parkinson's disease, Huntington's chorea and supranuclear palsy, and multi-infarct dementia; and painful degenerative disorders, such as fibromyalgia and reflex sympathetic dementia all involve the brain and/or nervous system and may be related to neurotransmitter activity.

In preferred embodiments of the new methods described and claimed herein, transcutaneous electrical nerve stimulation techniques are employed to treat, control and/or prevent these and other disorders. While the use of transcutaneous nerve stimulation for such purposes is not unknown, the particular new methods described herein are uniquely effective. For example, in preferred embodiments, the methods described herein result in increases in blood levels of neuro-transmitters, a heretofore unknown phenomenon. Most prior art transcutaneous nerve stimulators operate by delivering electrical stimulation to the body at a moderately low to very low frequency and at a single level of intensity. Usually, the patient is able to adjust either or both of the frequency and intensity, but the device then stimulates for the duration of the treatment at only those selected parameters. In contrast, the methods presented herein operate by stimulating, in a defined pattern, at a plurality of frequencies beginning at a very high frequency and sweeping through the plurality of frequencies to the lowest frequency, while maintaining the intensity of the stimulation at a single low intensity. Once a single sweep has been performed the intensity of the stimulation is incrementally increased and the entire frequency sweep performed at the new higher intensity.

In general, the frequency ranges that are preferred for the methods described and claimed herein are from about 60,000 Hertz to 100 Hertz, and most preferably from about 40,000 Hertz to 400 Hertz. This is in stark contrast to most transcutaneous electrical stimulating devices and methods which operate in the range of about 50 Hertz to 200 Hertz. Preferably, the duration of treatment at a single level of intensity, that is the time spent stimulating through a single sweep of frequency parameters, is 1 to 30 minutes. More preferably, the time is 1–20 minutes and most preferably 1–15 minutes. The range of acceptable stimulation intensities is not critical, but is generally from about zero to 100 volts, and in preferred embodiments is zero to 60 volts. The preferred stimulating device operates at about 40 mamps, but this too is not critical. What is important is that the general method of sweeping through the entire plurality of frequency parameters, along the frequency curve, occur for at least two sequentially increasing levels of intensity. Thus, for example, in a most preferred embodiment, as described further below, the maximum output voltage (intensity) of the device is equally divided into ten different intensity parameters (or levels); such as 5.7 volts at the lowest parameter (level 1), 10.4 volts at the second parameter (level 2), and so on up to 57 volts at the highest intensity parameter (level 10). While not all intensity levels are necessarily used in a single treatment program, those levels that are used are used for an entire, single sweep of the frequency curve.

Turning then to FIG. 1, illustrated is a block diagram of a preferred transcutaneous neurostimulator for use in practicing the improved methods described herein. This preferred transcutaneous nerve stimulation apparatus has digital frequency generation and provides two independent channels of bipolar, variable frequency, variable amplitude, and patient output signals. These output signals are coupled to the patient via skin electrodes, preferably two per channel. The frequency and amplitude of the outputs are preferably adjustable via front panel switches, or, in the case of frequency, also by a hand-held remote control. LED numeric and bar graph displays on the front panel may be used to provide the operator with a visual indication of amplitude (intensity) and frequency (bias) settings. The device is preferably battery powered and microprocessor controlled. Thus, the preferred apparatus is, conceptually, a two channel, variable frequency, variable amplitude, square wave frequency generator. As discussed in detail below, the apparatus preferably commences its operations at a highest frequency output and is reduced at a predefined rate, to a lowest frequency as other output parameters are increased (amplitude & current). This frequency sweep is preferably repeated over each of ten increasing intensity levels.

Preferably, the transcutaneous stimulator apparatus contemplated for use herein has five input/output connectors mounted on the back of the apparatus enclosure. These include, for example, an output connector for each channel, an input connector for battery charging, an input connector for the remote hand-held controller, and outputs for the treatment recorder. The battery employed in the apparatus is preferably a 12 volt, rechargeable gel cell. It supplies power for the entire system. It is recharged by connecting a wall mount charger to the charger input connector. Such a battery generally has a life of several hours depending, somewhat, upon the bias and amplitude settings used by the patient, as well as upon the individual patient load.

As contemplated herein, the front display of the apparatus is a membrane switch overlay with "smoked" transparent windows to allow display viewing. Displays include, for example, eight LED numeric digits and two 10 element LED bar graphs, with the following variables preferably being displayed: Channel 1 Intensity (2 digits plus decimal); Channel 1 Bias (2 digits plus decimal plus 10 bars); Channel 2 Intensity (2 digits plus decimal); and Channel 2 Bias (2 digits plus decimal plus 10 bars). Two additional LED elements are also preferably included on the front panel display, one indicating "Power On" and the other indicating "Battery Charging". Each channel preferably has five control switches: channel On/Off; Intensity Up; Intensity Down; Bias Up; and Bias Down. The membrane switch panel connects to the display board, which in turn connects to the microprocessor board. Via this connection, the microprocessor can detect when a front panel switch closure occurs and appropriately control the displays and patient output.

As shown in FIG. 1, a microprocessor board 20, containing the majority of the circuitry, is provided. The microprocessor 20 may be, for example, an 8 bit Motorola 68HC 11 device utilizing external EPROM 22 for program memory. The EPROM 22 memory preferably is about 8K bytes and is interfaced to the processor with an address latch and appropriate strobe decode logic. The processor clock preferably operates at about 8 MHZ and is crystal controlled. The processor communicates with the remaining circuitry via input/output ports, one of which includes an internal analog to digital converter. When the unit is switched on, the processor is momentarily at rest and then begins fetching and executing instructions from the EPROM memory. As long as the unit is switched on, the processor is running (fetching and executing instructions). The main functions of the processor are to read the operator control switches and remote hand-held controller, adjust the amplitude and frequency of the outputs, and send related data to the display board for display.

In the preferred embodiment, the On/Off switch and the emergency shut down switch relay 24 are in series with the positive pole of the 12 volt battery. Thus, when either of these switches are Off, no battery current flows to the microprocessor board. When On, 12 volts DC is supplied to the microprocessor board. The emergency shut down switch circuit employs an SCR to latch the relay in or out. Thus, once tripped this circuit is only reset by turning the main power off and then back on again.

The 12 volts is supplied primarily to three areas: a 5 volt regulator 26; a DC step up regulator 28; and a low battery detection circuit 30.

The 5 volt regulator 26 can be a standard linear, series, in-line regulator. The output is then a regulated 5 volts and provides the operating power supply for the majority of the circuitry (microprocessor, memory, display board, etc.). The DC step up regulator 28 is an inductive switching regulator used to increase the 12 volt DC input to an approximately 40 volt DC output. The switching regulator oscillates at a high frequency, varying with load. On one cycle of the oscillation, current passes through the inductor building up a magnetic field. On the alternate cycle the field collapses, inducing a high voltage which is stored in a large capture capacitor. The capture capacitor positive pole is the 40 volt output point and is fed back to the switching regulator circuit to cause a closed loop regulation of this voltage. The switching regulator varies frequency and duty cycle in order to maintain the output at 40 volts DC. This 40 volts is the supply voltage for the output stage intensity control amplifiers. A low battery detection circuit 30 is also provided. It determines when the 12 volt battery drops below a predetermined value, then trips the hardware interrupt on the processor and forces it to transition to a safe state and shut down. In addition, this is signaled to the operator by displaying "bA Lo" or similar informative message, on the display board 52.

One of the main functions of the processor is to monitor the user remote control 32 and front panel switches 34. The user remote control 32 is preferably a simple linear, slider potentiometer. It is connected across power (5+volts) and ground with its wiper forming the output. Thus, its output is a DC voltage somewhere between +5 volts and ground depending on wiper position. This signal is fed into an analog to digital converter input on the microprocessor. The A/D converter preferably has a resolution of 8 bits. Thus, the DC 0 to 5 volt input is converted to a digital number 0 to 255. This is then used by the processor to control the output bias setting (frequency). It should be noted that bias and frequency are inversely related; that is, a bias of 0.0 results in the highest frequency and a bias of 9.9 is the lowest frequency.

Each of the ten front panel switches are connected to an individual microprocessor port. The other side of all switches are connected to system ground. Also connected to each port is a pull up resistor to +5 volts. Thus, when the switches are open (unpressed), the port pins sit at +5 volts. When a switch is pressed, its associated port pin is forced to ground (0 volts). During operation of the preferred apparatus, the processor continually monitors these port pins, looking for a key press or change in remote control slider position. When detected, the appropriate action is taken.

A second important function of the processor in this preferred apparatus is to control the bias (frequency) and intensity (amplitude) of the outputs. The outputs are transformer-coupled to the patient. The patient is connected to the secondary side of a 1:1 transformer 46, 48 (one per channel). One lead of the primary side of the transformer is connected to the intensity drive circuitry 36, 38 and the other lead is connected to the bias drive circuitry 40, 42. The intensity drive circuitry 36, 38 is merely a DC voltage amplifier whose input in 0 to 5 volts, which is translated to 0 to 40 volts on the output. The input signal comes from a digital potentiometer 44 which is under control of the microprocessor 20. Thus, the processor 20 sends a digital byte to the digital potentiometer 44. The potentiometer 44 converts this into a voltage between 0 and 5 volts depending on the intensity setting. The intensity drive circuitry 36, 38 converts this into a voltage between 0 and 40 volts, which appears on one end of the transformer 46, 48 primary.

The bias drive circuitry 40, 42 is preferably a transistor power switch which pulls the other end of the transformer primary 46, 48 to ground when it is on, or lets it float (unconnected) when it is off. Thus when this switch is on, current flows through the primary at a level determined by the intensity setting (0 to 40 volts). When this switch is off, no current flows through the primary. The input to the bias drive circuitry is preferably a square wave created by a dual channel programmable timer 50. The timer is connected to the processor/memory bus and is programmed by the processor 20 to create a specific square wave frequency based on bias setting. The microprocessor "E Clock" forms the clock signal for the programmable timer (2 MHZ) 50. Thus, the processor 20 determines bias setting from front panel 34 switch presses and hand controller position 32. Using the bias setting the processor 20 determines desired frequency from a currently selected frequency look up table within the processor. The processor 20 then outputs the necessary commands to the programmable timer 50 to create a specific frequency output. It should be noted that since the frequency base to the timer is 2 MHZ, the resolution of frequency period is 0.5 micro seconds. The square wave output from the timer 50 then drives the digital switch which causes current to flow on and off, at the desired frequency, through the transformer primary. In other words, on one side of the transformer primary is a DC voltage, 0 to 40 volts, set by intensity; on the other side of the primary is an on/off switch, operating at the bias setting frequency. The processor 20 also preferably has an over riding "stop" line (not shown) to each channel which can force the bias drive circuitry off. In addition, while monitoring the hand controller 32 to determine bias setting the processor computes rate of change of hand controller position 32. If this rate of change exceeds a preset limit an error is detected and the outputs are switched off. This permits detection of, for example, a hand controller broken ground wire, or an accidentally moved (bumped) hand controller.

The display board 52 contains all the light emitting diode (LED) numeric and bar graph displays 54 in addition to the display drivers 56 and two input/output connectors (not shown). One connector mates with the membrane switch panel to bring front panel switch connections into the system. The other connector connects to a 20 pin ribbon cable which connects in turn to the microprocessor board. Power for the display board, front panel switch signals, and LED drive signals all flow through this ribbon cable.

Figure 2:
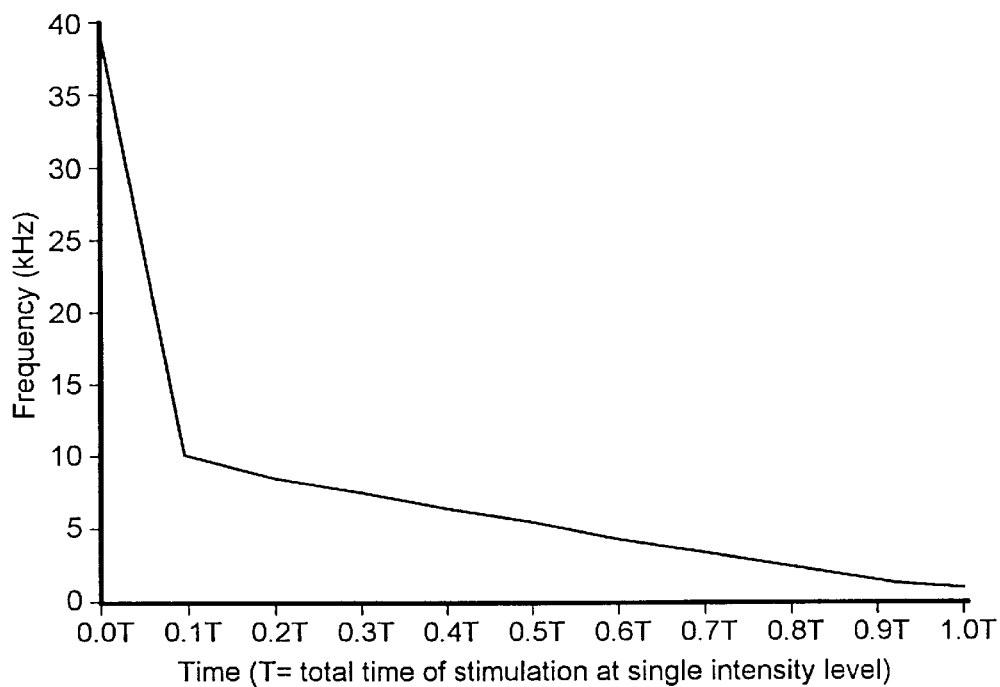
FIG. 2 is a schematic of a frequency curve preferred for use in treating tremor disorders.

Finally, in this most preferred embodiment of the apparatus, there are three driver integrated circuits on the display board. These provide direct drive for all the bar graph and numeric LED displays on the board. These drivers form a serial data link to the processor via the ribbon cable. Thus, the processor decides which LED's should be on and shifts out the appropriate serial data word to effect this. To conserve battery life the LED's are multiplexed on a 50% duty cycle, that is, at any one time, only half the LED's are on. This multiplex rate is faster than the human eye can perceive and thus the appearance is that all displays are constantly illuminated. To further conserve battery power the bar graph is preferably lighted in a climbing, one bar-at-a-time mode. All of the numeric, multiplexing, and bar graph decoding preferably takes place in the processor 20 under software control. The drivers merely turn on LED's bit for bit as instructed by the processor Referring now to FIG. 2, illustrated is a frequency curve preferred for use in treating tremor disorders, such as essential tremor and tremors associated with Parkinson's disease. It is this same curve, then, that is used at every intensity level at which stimulation is provided to the patient. Thus, at each intensity level, a range of stimulation frequencies is provided to the patient, beginning at about 40,000 Hz and decreasing to about 400 Hz, at the rate indicated by the frequency curve illustrated in FIG.2. The following detailed example is illustrative of a preferred treatment process for tremor disorders.

First, two pair of self-adhesive electrodes are affixed to the patient's skin. Suitable electrodes are well known to those of skill in the art, for example Bio-Skin Silver electrodes (Synaptic Corp., Aurora, Colo.). One pair is placed bilateral to the spine at C6, with approximately one inch between the inner medical borders of the electrodes. The second pair is affixed bilateral to the spine at L5, also spaced about one inch from one another as measured at the inner medical borders. Both pairs of electrodes are operatively attached to the electrical stimulator (i.e. pulse generator), which is most preferably preprogrammed with the desired treatment program thereby permitting the doctor, other medical or lay personnel or the patient his/herself to very easily activate the program. The next step is to turn on the electrical stimulator and begin the treatment program.

Generally, when the method is employed to treat, control or prevent a disorder selected from the group consisting of essential tremor and Parkinson's disease and wherein the step of incrementally decreasing the stimulation frequency parameter is performed for a time duration (T), one may employ the following sequential steps of a) steadily decreasing the stimulation frequency parameter about 70% over the time period 0.1T; b) steadily decreasing the stimulation frequency parameter about 5% over the time period 0.1T; c) steadily decreasing the stimulation frequency parameter about 20% over the time period 0.7T; and d) steadily decreasing the stimulation frequency parameter the remaining about 5% over the remaining time period of 0.1T, wherein the percentages are of the total frequency parameter range from the lowest frequency parameter to the highest frequency.

Electrical stimulation preferably begins at the highest stimulation frequency and lowest stimulation intensity for the programmed treatment. As illustrated in FIG. 2, the highest, and therefore initial, stimulation frequency is preferably about 40,000 Hz for treatment of tremor disorders. Preferably, the frequency curve of FIG. 2 is administered in a plurality of individual stimulation frequency parameters, and most preferably in about 100 different frequency parameters. These 100 different stimulation frequency parameters may, for example, be numbered as 0.0 through 9.9 (or 0.1 through 10.0). Preferred settings for some of the 100 points along the frequency curve illustrated in FIG. 2 are as follows:

TABLE C

| Frequency Parameter Number | Frequency (Hz) |
|---|---|
| 0.0 | 40,000 |
| 0.5 | 21,000 |
| 1.0 | 10,000 |
| 1.5 | 9,100 |
| 2.0 | 8,500 |
| 2.5 | 8,000 |
| 3.0 | 7,500 |
| 3.5 | 6,500 |
| 4.0 | 6,000 |
| 4.5 | 5,500 |
| 5.0 | 5,000 |
| 5.5 | 4,500 |
| 6.0 | 4,000 |
| 6.5 | 3,500 |
| 7.0 | 3,000 |
| 7.5 | 2,500 |
| 8.0 | 2,000 |
| 8.5 | 1,500 |
| 9.0 | 1,000 |
| 9.5 | 500 |
| 9.9 | 400 |

It is preferred to use at least about ten intensity levels, wherein the total output voltage available is equally divided among the ten (or more) levels. The maximum voltage output is not critical, but is preferably in the range of about 40–150 volts, and most preferably about 50–100 volts, peak to peak. A preferred tremor treatment program, in accordance with the present invention is about 45 minutes in duration, delivers stimulation according to the above described frequency curve and employs all 10 intensity levels according to the following schedule:

| Intensity Level | Time (minutes) |
|---|---|
| 1 | 1 |
| 2 | 2 |
| 3 | 2 |
| 4 | 4 |
| 5 | 4 |
| 6 | 4 |
| 7 | 4 |
| 8 | 8 |
| 9 | 8 |
| 10 | 8 |

At each intensity level, only one sweep of the stimulation frequency curve is performed. Thus, for example, at the lowest intensity level, level one, the stimulation frequency is reduced in one minute from about 40,000 Hz to about 400 Hz, following the curve illustrated in FIG. 2; whereas at intensity level 10, the highest intensity level, the stimulation frequency preforms the same pattern of decreasing from 40,000 to 400 Hz, but does so in eight minutes.

A patient, D.P., was treated in the manner just described, except that the highest stimulation frequency used was 30,000 Hz. D.P. had a ten year history of essential tremor. He suffered bilateral hand tremors. In his left hand, the tremors were so bad he could not touch his nose. While various drugs had brought D.P. some relief over the years, they slowly became ineffective, even at very high doses. D.P. was not a suitable candidate for implantation of a brain stimulator and thus, agreed to undergo this experimental transcutaneous electrical stimulation program. After his first 45-minute treatment, he remained tremor-free for four (4) hours. Daily treatments for the subsequent 14 days provided complete cessation of his tremors over each 24 hour period. D.P. has been receiving such treatment for over a year, and his tremors are still well controlled, despite receiving treatment only about three times a week. He has described the severity of his tremors as a 2 on a scale of 1–10 with 10 being the most severe tremors, and 1 being tremor-free.

Since beginning treatment on D.P., other patients suffering with tremor disorders have been treated on an experimental basis. The results, to date, have been consistent with those observed in D.P. Both bilateral hand tremors and head tremors (titubation) have been successfully treated using this new method and device. This is in stark contrast to the brain implant devices which have only been demonstrated useful in controlling tremors in one hand and not at all in the head. It is noted that, preferably, the patient (or doctor or other medical or lay personnel controlling the electrical stimulation) may stop the electrical stimulator at any time by pushing a single button. This control is important so that the patient does not experience unnecessary pain or discomfort during treatment.

It is believed that among other things, the general method of transcutaneous electrical stimulation described and claimed herein modulates both the ascending and descending pathways of the nervous system resulting in the release of neurotransmitters that then favorably affect the brain to control the symptoms of the disease being treated. In the case of treatment of tremor disorders, for example, it is believed that the thalamus and Basal Ganglion (the thalamocortical circuits) are stimulated by this method to provide control of both bilateral tremors and head tremors.

Figure 3:
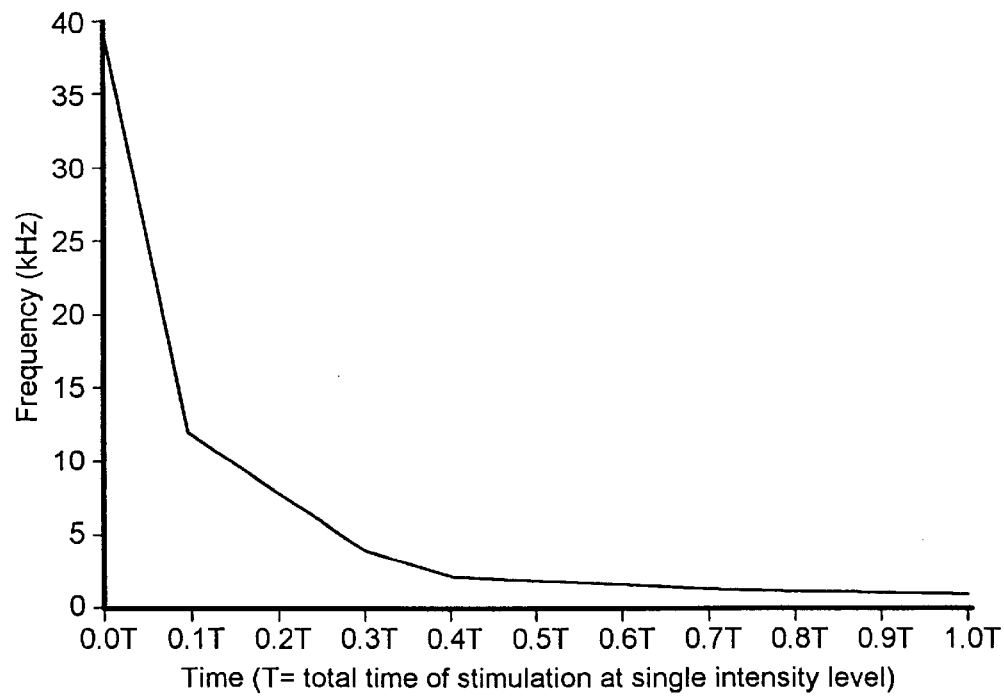
FIG. 3 is a schematic of an alternative frequency curve, preferred for use in treating dementia disorders and acute and chronic pain.
Figure 4:
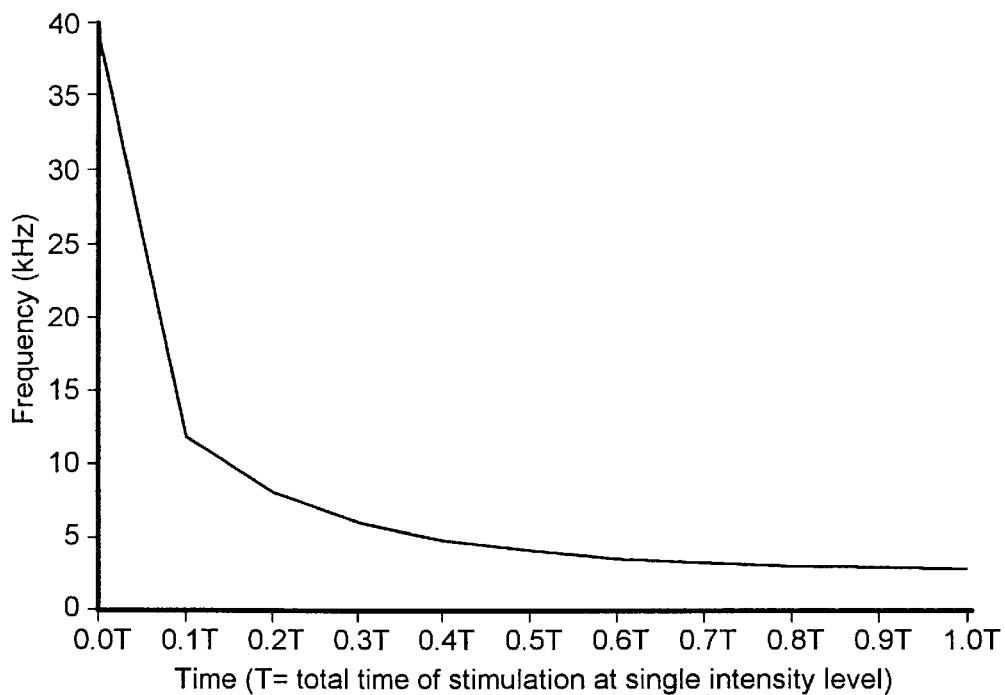
FIG. 4 is a schematic of an alternative frequency curve, preferred for use in treating painful degenerative disorders, such as fibromyalgia and reflex sympathetic dystrophy.
Figure 5:
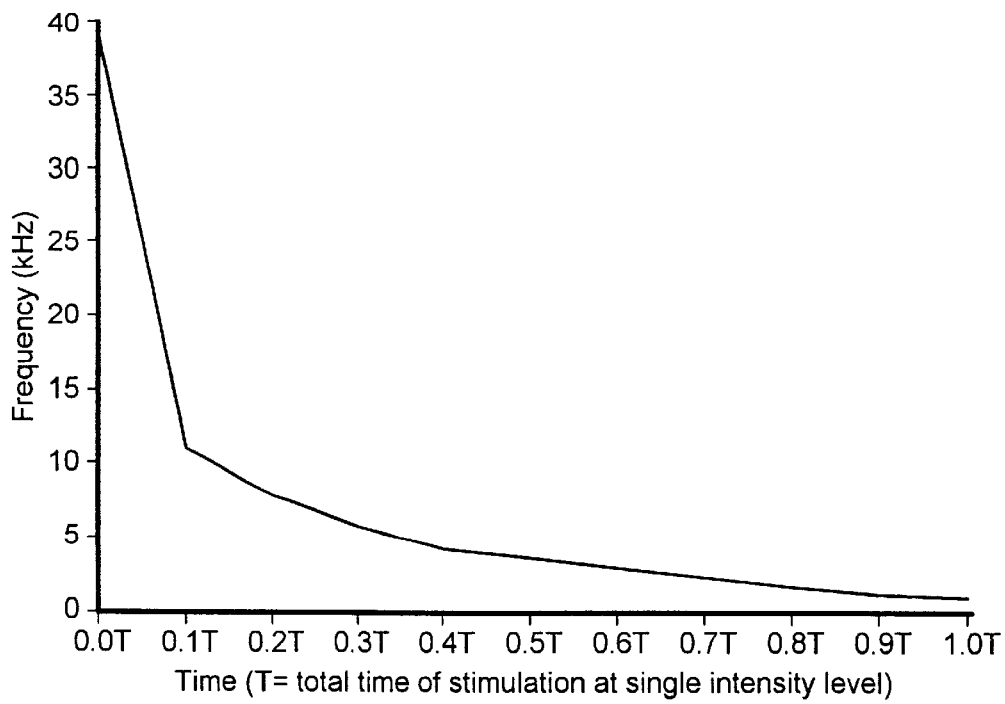
FIG. 5 is a schematic of an alternative frequency curve, preferred for use in treatment of pain and induction of electronic nerve block anesthesia and electroanesthesia.

FIGS. 3–5 each illustrate alternative, preferred frequency curves for treating various disease states and disorders. For example, FIG. 3 illustrates a frequency curve particularly useful for treating dementia disorders. FIG. 4 illustrates a frequency curve particularly suited to treatment of painful degenerative disorders such as fibromyalgia and reflex sympathetic dystrophy, and FIG. 5 is particularly useful for inducing electroanesthesia.

As with the method described above for treating tremor disorders, in preferred embodiments, the frequencies represented by these curves are administered as a plurality of frequency parameters and most preferably are administered as about 100 frequency parameters. Also in accordance with the general method of the present invention, a plurality of stimulation intensities are employed and the entire plurality of frequency parameters are administered at each intensity level.

For example, in treating a patient suffering with a dementia disorder, such as Alzheimer's disease, the patient first has two pairs of electrodes affixed to the skin in about the same location as described for treatment of tremor disorders; that is bilateral to the spine at C6 and L5. The leads of the electrodes are operatively connected to the electrical stimulator and the appropriate program initiated. As with the tremor treatment described above, the stimulation program to be used for treating the dementia patient is most preferably preprogrammed so that no adjustment thereto need be made by the patient (other than, of course, termination of the treatment should such be desirable or necessary). Once the electrodes are properly affixed to the patient and the leads connected to the electrical stimulator, the unit is switched on.

Generally, when the method is employed to treat, control or prevent a disorder selected from the group consisting of Alzheimer's disease, cortical dementia, subcortical dementia and multi-infarct dementia and wherein the step of incrementally decreasing the stimulation frequency parameter is performed for a time duration (T), one may employ the following sequential steps of a) steadily decreasing the stimulation frequency parameter about 66% over the time period 0.1T; b) steadily decreasing the stimulation frequency parameter about 23% over the time period 0.2T; c) steadily decreasing the stimulation frequency parameter about 5.5% over the time period 0.1T; and d) steadily decreasing the stimulation frequency parameter the remaining about 5.5% over the remaining time period of 0.6T, wherein the percentages are of the total frequency parameter range from the lowest frequency parameter to the highest frequency.

As previously described, stimulation always begins at the highest stimulation frequency parameter and lowest stimulation intensity. The program then decreases the stimulation from the highest frequency parameter, in this case, preferably about 40,000 Hz, to the lowest frequency parameter, preferably 400 Hz, in accordance with the frequency curve illustrated in FIG. 3. It is preferred that about 100 different frequency parameters be used. The following table provides settings for some of the 100 points along the frequency curve illustrated in FIG. 3:

| Frequency Parameter Number | Frequency (Hz) |
| --- | --- |
| 0.0 | 40,000 |
| 0.5 | 21,000 |
| 1.0 | 12,000 |
| 1.5 | 10,000 |
| 2.0 | 8,000 |
| 2.5 | 6,050 |
| 3.0 | 4,100 |
| 3.5 | 3,175 |
| 4.0 | 2,250 |
| 4.5 | 2,017 |
| 5.0 | 1,785 |
| 5.5 | 1,556 |
| 6.0 | 1,325 |
| 6.5 | 1,162 |
| 7.0 | 1000 |
| 7.5 | 900 |
| 8.0 | 800 |
| 8.5 | 700 |
| 9.0 | 600 |
| 9.5 | 500 |
| 9.9 | 400 |

A preferred treatment program for Alzheimer's disease, according to the present invention, involves slowly stepping up the maximum intensity of the stimulation over the course of several treatments. Thus, for example, during the first one-hour treatment administered to the patient, the stimulation intensity is raised only to level 7 of 10 (which is preferably 70% of the highest available intensity level). The one-hour treatments are preferably administered once a day, and this first level of treatment (i.e., wherein the maximum stimulation intensity is only 70% of the highest available intensity level) is preferably carried out for about the first ten days (or first ten one-hour treatments). The second level of treatment, preferably conducted for the $11^{th}$–$20^{th}$ of the daily treatments, increases the maximum intensity level to 8 (80% of the highest available intensity level). Treatments 21–30 provide a maximum intensity level of 9 (90%), and the remaining treatments include the highest available intensity level (10). The following table shows each of the four different levels of treatment with the number of one-hour treatments to be performed at that treatment level (in parentheses) and provides the duration of stimulation at each intensity level within each different level of treatment:

| Level 1 (1–10) | | Level 2 (11–20) | | Level 3 (21–30) | | Level 4 (31–) | |
| --- | --- | --- | --- | --- | --- | --- | --- |
| Intensity Level | Time (min) | Intensity Level | Time (min) | Intensity Level | Time (min) | Intensity Level | Time (min) |
| 1 | 1 | 1 | 1 | 1 | 1 | 1 | 1 |
| 2 | 2 | 2 | 2 | 2 | 2 | 2 | 2 |
| 3 | 4 | 3 | 4 | 3 | 4 | 3 | 4 |
| 4 | 8 | 4 | 8 | 4 | 8 | 4 | 8 |
| 5 | 15 | 5 | 10 | 5 | 8 | 5 | 8 |
| 6 | 15 | 6 | 10 | 6 | 8 | 6 | 8 |
| 7 | 15 | 7 | 10 | 7 | 9 | 7 | 8 |
| | | 8 | 15 | 8 | 10 | 8 | 8 |
| | | | | 9 | 10 | 9 | 8 |
| | | | | | | 10 | 5 |

While a specific rate for moving through the four levels of treatment is provided, this is meant to be illustrative only. Individual patients will tolerate the sensations associated with the transcutaneous stimulation differently. This is particularly of concern when dealing with Alzheimer's patients or other patients suffering from dementia, because such patients may be unable to communicate their level of comfort or discomfort clearly. Thus, the above schedule of treatment is intended as a guide. In practice, the doctor or other medical or lay personnel operating the device should closely monitor the patient for indications that he/she is becoming uncomfortable with the intensity of stimulation being administered. As with all the devices contemplated herein, it is preferred that the stimulation device include a simple mechanism for terminating stimulation, should such be desirable or necessary.

FIG. 4 illustrates a frequency curve preferred for use in treating painful degenerative disorders such as fibromyalgia and reflex sympathetic dystrophy, as well as general acute and chronic pain. Fibromyalgia is a widespread musculoskeletal pain and fatigue disorder for which the cause is still unknown. Most patients with fibromyalgia complain of systemic pain, often described as deep muscular aching, burning, throbbing, shooting and stabbing pain. No routine laboratory testing is available for diagnosing this debilitating disorder. Upon physical examination, patients are usually sensitive to pressure in certain areas of the body. Currently, diagnosis is made based solely on established criteria relating to the severity, widespread locality and duration of the pain.

Reflex sympathetic dystrophy (RSD) is a very severe form of chronic pain believed to affect as much as 10% of the entire population. The chronic pain of this syndrome is typified by a marked emotional connotation, such as severe anxiety, phobia and/or neuropsychological disturbances in the form of sever irritation, agitation and depression.

As with the specific examples given above for treatment of tremor and dementia disorders, treatment of fibromyalgia, RSD and similar painful degenerative disorders involves the administration of transcutaneous electrical stimulation beginning at a highest frequency parameter and lowest stimulation intensity level; decreasing the frequency parameter to a lowest frequency parameter by stimulating at a plurality of stimulation frequency parameters therebetween; then increasing the stimulation intensity level to a next highest intensity level and increasing the frequency parameter back to the highest parameter, followed by repeating the pattern of decreasing the frequency parameter to the lowest parameter. In a most preferred embodiment of treating these degenerative disorders, illustrated by the frequency curve of FIG. 4, the highest stimulation frequency parameter is 40,000 Hz and the lowest frequency parameter is 2,500 Hz. As with the previously described examples, the maximum output voltage is preferably divided into ten levels.

Generally, when the method is employed to treat, control or prevent a disorder selected from the group consisting of fibromyalgia, reflex sympathetic dystrophy, general acute pain and chronic pain and wherein the step of incrementally decreasing the stimulation frequency parameter is performed for a time duration (T), one may employ the following steps of a) steadily decreasing the stimulation frequency parameter about 66% over the time period 0.1T; b) steadily decreasing the stimulation frequency parameter about 13% over the time period 0.1T; c) steadily decreasing the stimulation frequency parameter about 6% over the time period 0.1T; d) steadily decreasing the stimulation frequency parameter about 5% over the time period 0.2T; and d) steadily decreasing the stimulation frequency parameter the remaining about 10% over the remaining time period of 0.5T, wherein the percentages are of the total frequency parameter range from the lowest frequency parameter to the highest frequency.

Thus, the following table provides several frequency parameters taken from the frequency curve illustrated in FIG. 4. As with the similar tables provided herein, the frequency parameters are preferably numbered 0.0 through 9.9, providing 100 different frequency parameters:

| Frequency Parameter Number | Frequency (Hz) |
| --- | --- |
| 0.0 | 40,000 |
| 0.5 | 21,000 |
| 1.0 | 12,000 |
| 1.5 | 9,875 |
| 2.0 | 7,750 |
| 2.5 | 6,775 |
| 3.0 | 5,800 |
| 3.5 | 5,275 |
| 4.0 | 4,750 |
| 4.5 | 4,375 |
| 5.0 | 4,000 |
| 5.5 | 3,760 |
| 6.0 | 3,520 |
| 6.5 | 3,360 |
| 7.0 | 3,200 |
| 7.5 | 3,100 |
| 8.0 | 3,000 |
| 8.5 | 2,850 |
| 9.0 | 2,900 |
| 9.5 | 2,600 |
| 9.9 | 2,500 |

Preferably, total treatment times are about 20 minutes and are, ideally, administered several times a week. However, weekly treatments have been demonstrated to provide noticeable favorable results. As with other treatments described herein, the treatment program typically begins with more time spent at lower intensities, gradually increasing the duration of stimulation at higher frequencies in subsequent treatments.

FIG. 5 illustrates a final exemplary frequency curve for use in accordance with the present invention. The frequency parameters comprising this curve have been found to be particularly useful in inducing electroanesthesia and nerve block anesthesia, as well as for the general treatment of pain. The following table provides exemplary frequency parameters taken from the curve illustrated in FIG. 5:

| Frequency Parameter Number | Frequency (Hz) |
| --- | --- |
| 0.0 | 40,000 |
| 0.5 | 25,500 |
| 1.0 | 11,000 |
| 1.5 | 9,500 |
| 2.0 | 8,000 |
| 2.5 | 7,000 |
| 3.0 | 6,000 |
| 3.5 | 4,750 |
| 4.0 | 4,500 |
| 4.5 | 4140 |
| 5.0 | 3,775 |
| 5.5 | 3,410 |
| 6.0 | 3,050 |
| 6.5 | 2,690 |
| 7.0 | 2,325 |
| 7.5 | 1,960 |
| 8.0 | 1,600 |
| 8.5 | 1,300 |
| 9.0 | 1,000 |
| 9.5 | 700 |
| 9.9 | 400 |

It will be apparent that where nerve block anesthesia (or electroanesthesia) is the goal, a single "treatment" is preferably performed. Generally, one pair of smaller electrodes, for example about 1.25 inches in diameter, are placed in the vicinity of the nerve to be blocked about 1 inch apart. A second pair of larger electrodes, for example about 2 inches in diameter, are placed about 1 inch apart either bilateral the spine at about C5 or on the opposite side of the body from the location of the first electrode pair. Stimulation is begun at a relatively high intensity and is manually increased as high as is reasonably tolerable to the patient, usually to a level of about 70%–90% of 60v maximum intensity of the neurostimulator described hereinbefore, i.e. about 40 to about 55v. The waveform employed has a fast rise time and a slow decay, which has been found to provide a particularly advantageous biological approach in that it stimulates the Action Potential responsible for producing electrical activity in human neurons. The intensity is then held at that level while the stimulation frequency is decreased to a lower frequency. The original decrease in frequency may be carried out in a manner that can be accommodated by the patient to reach an initial tolerable stimulation level, with the frequency level being decreased increment by increment thereafter. Alternatively, the program is used which is set to sweep through a plurality of frequencies in accordance with the curve set forth in FIG. 5 that is depicted in the table set just above, usually for a period of at least about 20 minutes and often from 20 to 30 minutes. It is noted that, either a single frequency parameter sweep may be performed or at the end of a first sweep, the treatment may be repeated at a next higher intensity level.

Generally, when the method of treatment is employed to create a nerve block by electroanesthesia, one may incrementally decrease the stimulation frequency parameter for a time duration (T) as exemplified in FIG. 5 by employing the following steps of (a) continuously decreasing the stimulation frequency about 73% of the first high frequency over the first time period 0.1T; (b) continuously decreasing the stimulation frequency about another 8% of the first high frequency over the next time period 0.1T; (c) continuously decreasing the stimulation frequency about another 5% of the first high frequency over the next time period 0.1T; (d) continuously decreasing the stimulation frequency about another 4% of the first high frequency over the next time period 0.1T; and (e) continuously decreasing the stimulation frequency about another 10% over the remaining time period of 0.6T.

As can be seen from the Figures herein, the frequency curves have a similar basically logarithmic shape. Association of specific frequency parameters and curve slopes with a specific disorder is preferably determined by clinical evaluation. In fact, the different curves exemplified herein are useful for treating other diseases and disorders. Thus, it is the particular manner of stimulating described herein that makes these methods particularly effective, that is the stimulating manner of sweeping through the same set of frequency parameters from a high frequency parameter of, for example, 40,000 Hz, to a low frequency of, for example 400 Hz, at each of a plurality of incrementally increasing stimulation intensities.

It is believed that the required initial stimulation at a high frequency causes rapid depolarization of the cell permitting ideal functioning of the so stimulated neurons. Whereas prior art TENS devices and methods are believed to stimulate only the large Aβ fibers of the nervous system, it is believed that the present method results in stimulation of the Aδ and C fibers as well as the Aβ fibers, by providing stimulation waveforms that closely mimic natural action potential waveforms and/or piggyback on such waveforms. Increases in circulating blood levels of various neurotransmitters, such as norepinephrine, serotonin, epinephrine, ACTH and beta endorphins, provide evidence of this mode of operation.

Figure 6:
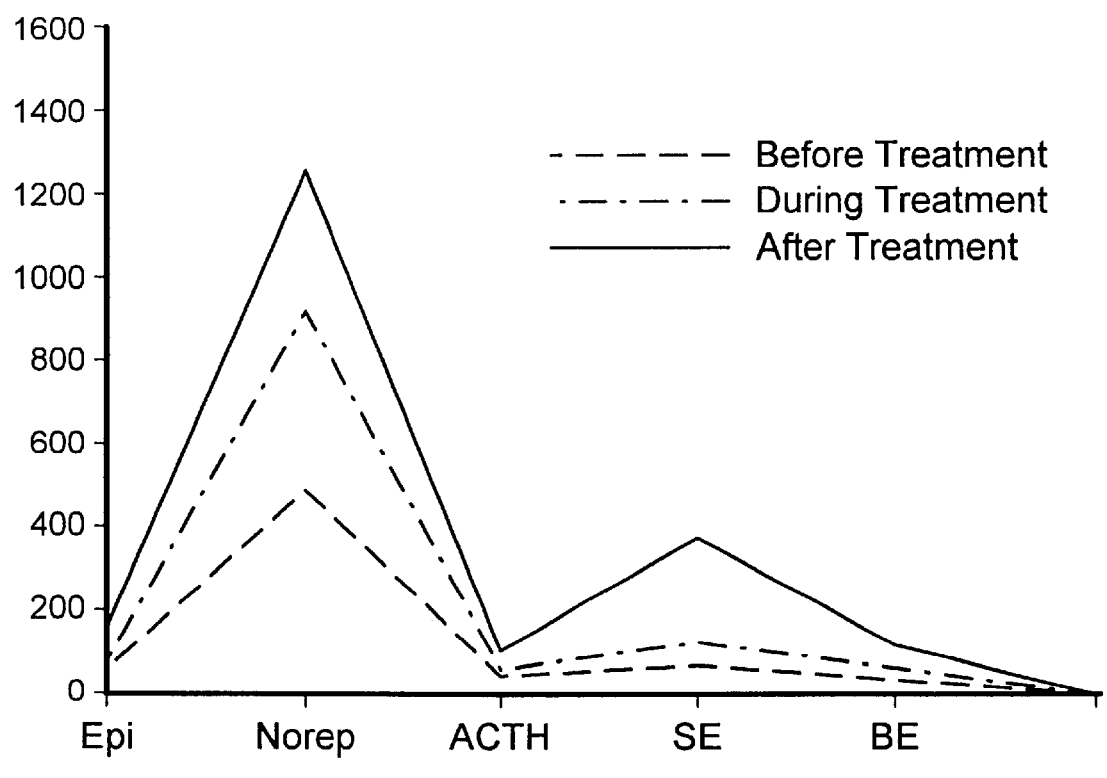
FIG. 6 is a graph of results of neurochemical blood assays taken from a patient before, during and twenty-four hours following treatment in accordance with the methods herein.

As seen in FIG. 6, in one patient, suffering with chronic pain, the levels of various neurotransmitters not only increased during the 20 minute treatment provided, but continued to measurably increase for the 24 hours following such treatment. Note that the y-axis scale on the graph in FIG. 6 is relativistic. Levels of the neurotransmitters are measured in pg/ml for epinephrine and norepinephrine, in pmol/l for ACTH, in ng/ml for serotonin and in pg/0.1 ml for beta endorphin. Thus, the graph should be used to compare levels of a single neurotransmitter over time not to compare levels among neurotransmitters. Thus, by providing electrical stimulation at a central location on the body, in accordance with the methods detailed herein, the body's natural healing mechanisms are systemically stimulated to relieve the symptoms of the nerve-related disease condition being treated.

The examples provided herein are of specific embodiments only and are not intended to limit the scope of the claims appended hereto. Those of skill in the art will recognize that the preferred embodiments described herein may be altered or amended without departing from the true spirit and scope of the invention, as defined in the following claims.

What is claimed is:

1. A non-invasive method of inducing nerve blocks by using electroanesthesia applied via transcutaneous electrical stimulation, which method comprises affixing a first electrode pair to the skin of a patient to be treated in the vicinity of the nerve to be blocked, which electrode pair is associated with a pulse generator such that stimulation at a desired frequency and intensity may be provided to the patient through said electrode pair, affixing a second electrode pair to the skin of a patient either on the opposite side of the body from the location of the first electrode pair or bilaterally of the spine at about C5, said second electrode pair being larger in size than said first electrode pair and also being associated with the pulse generator, and thereafter carrying out the following steps of:
(a) providing the patient with a series of intensities at which stimulation may be carried out;
(b) choosing an intensity from said series as high as the patient can reasonably tolerate;
(c) stimulating at a first high frequency in the range of 60,000 Hz to about 25,000 Hz and at said chosen intensity; and
(d) decreasing the stimulation frequency at said chosen intensity to a lower frequency over a time period of at least about 20 minutes by initially lowering the frequency to a level that is still tolerable to the patient and then continuing to gradually decrease the frequency thereafter.

2. The method of claim 1 wherein said first high intensity is between about 55 and about 40 volts.

3. The method of claim 2 wherein the first high frequency parameter is about 40,000 Hertz and the lowest frequency parameter is not less than about 250 Hertz.

4. The method of claim 2 wherein said first high intensity is at an amperage of about 40 milliamps.

5. The method of claim 2 wherein said stimulating employs a waveform having a fast time rise and a slow decay.

6. The method of claim 2 wherein the first high frequency parameter is about 40,000 Hertz and the lowest frequency parameter is not less than about 400 Hertz.

7. The method of claim 1 wherein said second electrode pair is located bilateral of the spine at C5.

8. The method of claim 1 wherein said decreasing of the stimulation frequency is performed over a time duration (T) of at least about 20 minutes and comprises the steps of:

a) decreasing the stimulation frequency about 73% of the first high frequency over the first time period 0.1T;

b) then decreasing the stimulation frequency about another 8% of the first high frequency over the next time period 0.1T;

c) then decreasing the stimulation frequency about another 5% of the first high frequency over the next time period 0.1T;

d) then decreasing the stimulation frequency about another 4% of the first high frequency over the next time period 0.1T; and e) then decreasing the stimulation frequency about another 10% over the remaining time period of 0.6T.

9. The method of claim 8 wherein the first high frequency parameter is about 40,000 Hertz and the lowest frequency parameter is not less than about 400 Hertz.

10. The method of claim 9 wherein said first high intensity is between about 55 and about 40 volts at an amperage of about 40 milliamps.

* * * * *